United States Patent
Schulze zur Wiesche et al.

(10) Patent No.: US 10,653,599 B2
(45) Date of Patent: May 19, 2020

(54) HAIR TREATMENT AGENT WITH A POLYVALENT CATION II

(71) Applicant: Henkel AG & Co. KGaA, Duesseldorf (DE)

(72) Inventors: Erik Schulze zur Wiesche, Hamburg (DE); René Krohn, Norderstedt (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 16/117,928

(22) Filed: Aug. 30, 2018

(65) Prior Publication Data
US 2019/0070084 A1 Mar. 7, 2019

(30) Foreign Application Priority Data
Sep. 5, 2017 (DE) .................. 10 2017 215 578

(51) Int. Cl.
*A61K 8/365* (2006.01)
*A61K 8/20* (2006.01)
*A61K 8/362* (2006.01)
*A61Q 5/12* (2006.01)

(52) U.S. Cl.
CPC ............... *A61K 8/365* (2013.01); *A61K 8/20* (2013.01); *A61K 8/362* (2013.01); *A61Q 5/12* (2013.01)

(58) Field of Classification Search
CPC . A61K 8/19; A61K 8/20; A61K 8/365; A61K 8/36; A61K 8/362; A61Q 5/002; A61Q 5/065; A61Q 5/10; A61Q 5/12
See application file for complete search history.

(56) References Cited

U.S. PATENT DOCUMENTS

| | | | | |
|---|---|---|---|---|
| 4,201,235 A | * | 5/1980 | Ciavatta | A61K 8/44 132/202 |
| 4,834,971 A | | 5/1989 | Klenk et al. | |
| 6,231,843 B1 | * | 5/2001 | Hoelzel | A61K 8/365 424/70.1 |
| 2002/0031556 A1 | * | 3/2002 | Lindahl | A61K 9/0014 424/616 |
| 2017/0360674 A1 | * | 12/2017 | Schulze zur Wiesche | A61K 8/26 |

FOREIGN PATENT DOCUMENTS

| | | | | |
|---|---|---|---|---|
| CN | 101066093 A | * | 11/2007 | |
| CN | 106420499 A | | 2/2017 | |
| FR | 2937539 A1 | * | 4/2010 | A61K 8/19 |
| GB | 2557378 A | | 6/2018 | |
| JP | 2009007283 A | | 1/2009 | |
| WO | WO-2016096267 A1 | * | 6/2016 | A61K 8/26 |

OTHER PUBLICATIONS

CN-101066093-A, Espacenet English translation, downloaded 2019 (Year: 2019).*
FR-2937539-A1, Espacenet English translation, downloaded 2019 (Year: 2019).*

* cited by examiner

*Primary Examiner* — Mark V Stevens
(74) *Attorney, Agent, or Firm* — Lorenz & Kopf, LLP

(57) ABSTRACT

The present disclosure relates to a hair treatment agent for reducing and/or avoiding bleeding out and/or fading of artificially produced hair colours with a pH in a range of from about 3.5 to about 5 containing—relative to the total quantity of hair treatment agent— a) from about 0.01 to about 10 wt. % of a polyvalent metal salt, wherein the metal salt is selected from the group of strontium salts, zirconium salts, hafnium salts, titanium salts, tin salts, aluminium salts, bismuth salts, lanthanum maleate, lanthanum chloride and mixtures thereof and b) from about 0.01 to about 10 wt. % of an organic acid selected from the group of tartaric acid, citric acid, maleic acid, fumaric acid, salicylic acid, lactic acid, malic acid, amino acids and mixtures thereof.

19 Claims, No Drawings

HAIR TREATMENT AGENT WITH A POLYVALENT CATION II

CROSS-REFERENCE TO RELATED APPLICATION

This application claims priority to German Patent Application No. 10 2017 215 578.7, filed Sep. 5, 2017, which is incorporated herein by reference in its entirety.

TECHNICAL FIELD

The application relates to hair treatment agents for strengthening the internal hair structure with a polyvalent cation.

BACKGROUND

Hair can be damaged by natural or artificially induced processes. The most important type of damage here can be oxidative damage.

The natural processes can for example comprise a combined (e.g. simultaneous) action of UV light and oxygen ($O_2$) on the hair.

The artificially induced processes can for example comprise an application of hair colourants (also designated as colourations), dying blond and/or producing a permanent wave. In particular, hair colourants play a prominent role in hair cosmetics.

In this case, in addition to desired cosmetic effects such as, for example, a lightening of the hair, severe damage to the hair can also occur, for example, when using oxidants.

The damage process here can take place causatively by oxidation of amino acids, for example, oxidation of the amino acids cystine and cysteine which occur very frequently in hair to give cysteic acid. Cystine can form intermolecular disulphide bridges (also designated as S-S bridges) in the hair so that the cysteine is extremely important for the mechanical stability of the hair.

The oxidation of these bridges to give cysteic acid can destroy the mechanical stability of the hair and in many applications can even result in a complete breaking of the hair. A loss of mechanical stability can result in an intensified swelling of the hair in water.

However, properties of the hair which were already previously macroscopically perceptible, e.g. sensible, for example, a surface roughness can be negatively influenced.

BRIEF SUMMARY

Hair treatment agents and methods for strengthening the internal hair structure are provided herein. In an embodiment, a hair treatment agent for strengthening the internal hair structure has a pH in a range of from about 3.5 to about 5. The hair treatment agent includes, relative to the total quantity of hair treatment agent, from about 0.01 to about 10 wt. % of a polyvalent metal salt and from about 0.01 to about 10 wt. % of an organic acid. The metal salt is selected from the group of strontium salts, zirconium salts, hafnium salts, titanium salts, tin salts, aluminium salts, bismuth salts, lanthanum maleate, lanthanum chloride, and mixtures thereof. The organic acid is selected from the group of tartaric acid, citric acid, maleic acid, fumaric acid, salicylic acid, lactic acid, malic acid, amino acids, and mixtures thereof.

In another embodiment, a method for strengthening the internal hair structure includes applying a hair treatment agent to dyed-blond or oxidatively coloured hair and letting the agent act for a period of at least about 5 seconds. Optionally, the composition is rinsed out of the hair with water. The hair treatment agent has a pH in the range of from about 3.5 to about 5 and includes, relative to its weight from about 0.01 to about 10 wt. % of a polyvalent metal salt and from about 0.01 to about 10 wt. % of an organic acid. The metal salt is selected from the group of strontium salts, zirconium salts, hafnium salts, titanium salts, tin salts, aluminium salts, bismuth salts, lanthanum maleate, lanthanum chloride, and mixtures thereof. The organic acid is selected from the group of tartaric acid, citric acid, maleic acid, fumaric acid, salicylic acid, lactic acid, malic acid, amino acids and mixtures thereof.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was the object of the present disclosure to provide a hair treatment agent which, in particular in the case of oxidatively damaged hair, is able to reconstruct the damaged intermolecular bonds in the hair fibres and thus strengthen the internal hair structure.

It was found that a hair treatment agent which, in addition to a polyvalent metal salt, contains a selected organic acid and has a pH in the range of from about 3.5 to about 5 is exceptionally suitable for this.

A first subject matter of the present disclosure is therefore a hair treatment agent for strengthening the internal hair structure with a pH in a range of from about 3.5 to about 5 containing—relative to the total quantity of hair treatment agent— a) from about 0.01 to about 10 wt. % of a polyvalent metal salt, wherein the metal salt is selected from the group of strontium salts, zirconium salts, hafnium salts, titanium salts, tin salts, aluminium salts, bismuth salts, lanthanum maleate, lanthanum chloride and mixtures thereof and b) from about 0.01 to about 10 wt. % of an organic acid selected from the group of tartaric acid, citric acid, maleic acid, fumaric acid, salicylic acid, lactic acid, malic acid, amino acids and mixtures thereof.

Suitable hair treatment agents are preferably hair washing agents such as shampoos, hair care agents such as hair conditioners, rinses or hair care sprays as well as hair styling agents such as hair gels, hair sprays or hair wax. Particularly preferably the hair treatment agent comprises a shampoo or a hair care agent. It is particularly preferable that the hair care agent is used following a dyeing blond or oxidative colouring of the hair.

The hair treatment agent necessarily contains a polyvalent metal salt, wherein the metal salt is selected from the group of strontium salts, zirconium salts, hafnium salts, titanium salts, tin salts aluminium salts, bismuth salts, lanthanum maleate, lanthanum chloride and mixtures thereof. Preferably the hair treatment agents contain a tri- or tetravalent metal salt, in particular an aluminium salt, a zirconium salt, lanthanum maleate, lanthanum chloride or a mixture thereof.

Particularly preferred polyvalent metal salts comprise lanthanum maleate, lanthanum chloride, an aluminium salt or a mixture thereof.

In a particularly preferred embodiment the hair treatment agent contains as polyvalent metal salt, lanthanum maleate, lanthanum chloride and/or aluminium lactate.

In a quite particularly preferred embodiment the hair treatment agent contains as polyvalent metal salt lanthanum maleate and/or aluminium lactate.

The hair treatment agents contain—relative to their weight—preferably from about 0.1 to about 7.5 wt. % and more preferably from about 0.5 to about 5 wt. % of a polyvalent metal salt, preferably of lanthanum maleate, lanthanum chloride and/or aluminium lactate and more preferably of lanthanum maleate and/or aluminium lactate.

The hair treatment agents contain as second essential ingredient—relative to their weight—from about 0.01 to about 10 wt. % of a selected organic acid.

The organic acid is selected from the group of tartaric acid, citric acid, maleic acid, fumaric acid, salicylic acid, lactic acid, malic acid, amino acids and mixtures thereof. Suitable amino acids comprise glycine, glutamic acid, arginine and/or asparagic acid. Particularly preferably lactic acid and/or maleic acid are used as organic acid.

The hair treatment agents contain the organic acid preferably in a quantity of from about 0.1 to about 5 wt. % and particularly preferably from about 0.5 to about 3 wt. %, in each case relative to the weight of the ready-to-use hair treatment agent.

The organic acids are used on the one hand to adjust the pH of the hair treatment agent to a value between from about 3.5 and about 5 and in a preferred embodiment the hair treatment agent has a pH in the range of from about 3.75 to about 4.75.

It has been shown that the use of a selected organic acid combined with a polyvalent salt imparts exceptionally good properties to the hair treatment agents. In particular, the hair treated with these hair treatment agents has a stronger internal structure which is shown in a higher denaturing temperature, an increased tearing strength and a reduced swelling in water. This applies in particular to the application to oxidatively damaged hair.

It was found that it is particularly effective and the strengthening of the internal structure is particularly high if the hair treatment agents contain lanthanum maleate and maleic acid, lanthanum chloride and lactic acid or aluminium lactate and lactic acid.

The hair treatment agent further preferably contains an aqueous or an aqueous alcohol carrier. An aqueous carrier contains at least about 50 wt. % of water. Aqueous alcohol carriers are to be understood in the sense of the present disclosure as aqueous solutions containing from about 3 to about 70 wt. % of a $C_2$-$C_6$-alcohol, in particular ethanol or propanol, isopropanol, butanol, isobutanol, tert.-butanol, n-pentanol, iso-pentanols, n-hexanol, iso-hexanols, glycol, glycerin, 1,2-pentanediol, 1,5-pentanediol, 1,2-hexanediol or 1,6-hexanediol. The agents can additionally contain further organic solvents such as, for example methoxybutanol, benzylalcohol, ethyldiglycol or 1,2-propyleneglycol. Preferred here are all water-soluble organic solvents.

The hair treatment agent can in principle be applied to any hair. However, it is particularly advantageous to apply the hair treatment agent to damaged hair, in particular oxidatively damaged hair. Oxidatively damaged hair is in particular hair which has a cysteic acid content greater than about 1 wt. %. Accordingly the hair treatment agents are particularly suitable for application to dyed-blond or oxidatively damaged hair.

In addition to the aforesaid ingredients, the hair treatment agents can contain further ingredients which are usual in the respective agents.

If the hair treatment agent is produced as a hair shampoo, it preferably contains a selected anionic tenside.

The group of selected anionic tensides include alkyl (ether)sulphates, sulphosuccinates, ethercarboxylic acid, acylglutamate and/or (acyl)isethionate each having from about 8 to about 24 C atoms in the acyl group as well as mixtures of these tensides. Preferred anionic tensides comprise for example:

Ethercarboxylic acids having the formula R—O—$(CH_2$—$CH_2O)_x$—$CH_2$—COOH, where R is a linear or branched, saturated or unsaturated alkyl group with from about 8 to about 30 C atoms and x=0 or from 1 to about 16, N-acylamino acids with from about 8 to about 24 C atoms in the acyl group, (Acyl)isethionate with from about 8 to about 24 C atoms in the acyl group, Sulphosuccinic acid mono- and/or -dialkylesters with from about 8 to about 24 C atoms in the alkyl group and sulphosuccinic acid mono-alkylpolyoxyethylesters with from about 8 to about 24 C atoms in the alkyl group and from 1 to about 6 oxyethyl groups and/or Alkylsulphate and/or alkylpolyglycolether sulphate salts having the formula R—$(OCH_2$—$CH_2)_x$—$OSO_3^-X^+$, where R is preferably a linear or branched, saturated or unsaturated alkyl group with from about 8 to about 30 C atoms, x is a number 0 or from 1 to about 12 and X is an alkali, alkaline earth, ammonium or alkanolamine ion.

Particularly preferred anionic tensides are straight-chain or branched alkylether sulphates having the afore-mentioned formula which contain an alkyl group with from about 8 to about 18, in particular with from about 10 to about 16 C atoms as well as from 1 to about 6 and in particular from about 2 to about 4 ethylene oxide units. Particularly preferably the sodium, magnesium and/or triethanolamine salts are linear or branched lauryl, tridecyl and/or myristylsulphates, which have a degree of ethoxylation of from about 2 to about 4.

If the hair treatment agent is produced as a hair shampoo, it preferably contains at least one anionic tenside in a preferred weight fraction of from about 0.5 to about 20 wt. %, more preferably of from about 1 to about 15 and particularly preferably of from about 2 to about 12 wt. %, wherein the quantitative information is relative to the total weight of the hair treatment agent.

If the hair treatment agent is produced as rinse, hair conditioner or care spray, it preferably contains a cationic tenside.

The cationic tensides in particular comprise quaternary ammonium compounds, esterquats and/or amidoamines.

Preferred quaternary ammonium compounds are ammonium halides, in particular chlorides or bromides such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride, as well as the imidazolinium compounds known under the INCI designations Quaternium-27, Quaternium-83 and Quaternium-87. The alkyl chains of the aforesaid tensides preferably have from about 10 to about 18 carbon atoms.

Esterquats are substances which contain both at least one ester function and also at least one quaternary ammonium group as structural element. Preferred esterquats are quaternated ester salts of fatty acids with triethanol amine, quaternated ester salts of fatty acids with diethanol alkylamines and quaternated ester salts of fatty acids with 1,2-dihydroxypropyl dialkylamines. Specific examples are methyl-N-(2-hydroxyethyl)-N,N-di(talgacyloxyethyl)ammonium compounds, bis-(palmitoyloxyethyl)hydroxyethyl-methyl-ammonium compounds, methyl-N,N-bis(stearoyloxyethyl)-N-(2-hydroxyethyl)ammonium compounds, methyl-N,N-bis(cocoyloxyethyl)-N-(2-hydroxyethyl)ammonium compounds or N,N-dimethyl-N,N-di(talgacyloxyethyl)ammonium compounds. Such products are marketed under the designations Stepantex®, Dehyquart®, Armocare® and Quartamin®.

Alkyl amidoamines are usually produced by amidization of natural or synthetic fatty acids and fatty acid sections with dialkyl aminoamines. A particularly suitable compound from this substance group is the stearamidopropyl dimethylamine available commercially under the designation Tego-amid® S 18.

The quantity of cationic tenside is preferably a maximum of about 2 wt. % relative to the total weight of the hair treatment agent.

The hair treatment agents can contain at least one hair-conditioning active substance in a weight fraction of from about 0.01 to about 10 wt. % of the total weight of the hair treatment agent. Suitable hair-conditioning active substances are preferably understood as cationic care polymers, natural, mineral or synthetic oil, fat or wax components, vitamins and/or protein hydrolysates. By using a cationic polymer, preferably a cationic polysaccharide and/or a plant oil and/or a silicone as hair-conditioning active substance, in particular the haptic properties such as the hold and the sleekness of the hair can be improved.

Further suitable ingredients comprise non-ionic tensides, amphoteric/zwitterion tensides, non-ionic polymers, anionic polymers, amino acids, oligopeptides, provitamins, vitamin precursors, betaine, bioquinone, purine(derivatives), taurine (derivatives), L-carnitine(salts), panthenol, panthothenic acid, 2-furanone, 2-furanone derivatives, ectoine, allantoine, plant extracts, ester oils, UV-light protection filters, structuring agents, thickeners, electrolytes, pH-regulating agents, expanding agents, dyes, anti-dandruff agents, complex forming agents, opacifiers, pearl shine agents, pigments, stabilizing agents, propellants, antioxidants, perfumed oils, and/or preserving agents.

Preferred hair treatment agents are exemplified as follows:
from about 0.1 to about 7.5 wt. % of a tri- or tetravalent metal salt which comprises zirconium salts, hafnium salts, titanium salts, tin salts, aluminium salts, bismuth salts, lanthanum maleate and/or lanthanum chloride,
from about 0.1 to about 5.0 wt. % of an organic acid selected from the group of tartaric acid, citric acid, maleic acid, fumaric acid, salicylic acid, lactic acid, malic acid, amino acids and mixtures thereof and
a pH in the range of from about 3.5 to about 5.

Further preferred hair treatment agents are exemplified as follows:
from about 0.5 to about 5.0 wt. % of a trivalent metal salt which comprises zirconium salts, aluminium salts, lanthanum maleate and/or lanthanum chloride,
from about 0.5 to about 20.0 wt. % of at least one anionic tenside selected from the group formed from alkyl(ether) sulphates, sulphosuccinates, ethercarboxylic acids, N-acylamino acids with from about 8 to about 24 C atoms in the acyl group, (acyl)isethionates with from about 8 to about 24 C atoms in the acyl group and mixtures of these tensides,
from about 0.1 to about 5.0 wt. % of an organic acid selected from the group of tartaric acid, citric acid, maleic acid, fumaric acid, salicylic acid, lactic acid, malic acid, amino acids and mixtures thereof and
a pH in the range of from about 3.5 to about 5.

Still further preferred hair treatment agents are exemplified as follows:
from about 0.5 to about 5.0 wt. % of a trivalent metal salt which comprises aluminium salts, lanthanum maleate and/or lanthanum chloride,
from about 0.5 to about 20.0 wt. % of at least one anionic tenside selected from the group formed from alkyl(ether) sulphates, sulphosuccinates, ethercarboxylic acids, N-acylamino acids with from about 8 to about 24 C atoms in the acyl group, (acyl)isethionates with from about 8 to about 24 C atoms in the acyl group and mixtures of these tensides,
from about 0.1 to about 5.0 wt. % of an organic acid selected from the group of tartaric acid, citric acid, maleic acid, fumaric acid, salicylic acid, lactic acid, malic acid, amino acids and mixtures thereof and
a pH in the range of from about 3.75 to about 4.75.

Within this embodiment, extraordinarily preferred are hair treatment agents which are exemplified as follows:
from about 0.5 to about 5.0 wt. % of a trivalent metal salt containing aluminium lactate, lanthanum chloride and/or lanthanum maleate,
from about 0.5 to about 20.0 wt. % of at least one anionic tenside selected from the group formed from alkyl(ether) sulphates, sulphosuccinates, ethercarboxylic acids, N-acylamino acids with from about 8 to about 24 C atoms in the acyl group, (acyl)isethionates with from about 8 to about 24 C atoms in the acyl group and mixtures of these tensides,
from about 0.5 to about 3.0 wt. % of an organic acid selected from the group of maleic acid, lactic acid and mixtures thereof
from about 0.01 to about 10 wt. % of a cationic polysaccharide and
a pH in the range of from about 3.75 to about 4.75.

Likewise preferred hair treatment agents are those which contain, instead of the cationic polysaccharide, a natural, mineral or synthetic oil, fat or wax component, in particular from about 0.01 to about 10 wt. % of at least one plant oil and/or a silicone as a hair-conditioning active substance.

Alternative, likewise further preferred hair treatment agents are exemplified as follows:
from about 0.5 to about 5.0 wt. % of a trivalent or tetravalent metal salt which comprises zirconium salts, hafnium salts, titanium salts, tin salts, aluminium salts, bismuth salts, lanthanum maleate and/or lanthanum chloride,
from about 0.1 to about 10.0 wt. % of a cationic tenside selected from the group formed from quaternary ammonium compounds, esterquats and/or amidoamines and mixtures of these tensides,
from about 0.1 to about 5.0 wt. % of an organic acid selected from the group of tartaric acid, citric acid, maleic acid, fumaric acid, salicylic acid, lactic acid, malic acid, amino acids and mixtures thereof and
a pH in the range of from about 3.5 to about 5.

Alternative, likewise further preferred hair treatment agents are exemplified as follows:
from about 0.5 to about 5.0 wt. % of a trivalent metal salt which comprises aluminium salts, lanthanum maleate and/or lanthanum chloride, from about 0.1 to about 10.0 wt. % of a cationic tenside selected from the group formed from quaternary ammonium compounds, esterquats and/or amidoamines and mixtures of these tensides, from about 0.1 to about 5.0 wt. % of an organic acid selected from the group of tartaric acid, citric acid, maleic acid, fumaric acid, salicylic acid, lactic acid, malic acid, amino acids and mixtures thereof and a pH in the range of from about 3.75 to about 4.75.

Within this embodiment, extraordinarily preferred are hair treatment agents which are exemplified as follows:

from about 0.5 to about 5.0 wt. % of a trivalent metal salt containing aluminium lactate, lanthanum chloride and/or lanthanum maleate, from about 0.1 to about 10.0 wt. % of a cationic tenside selected from the group formed from quaternary ammonium compounds, esterquats and/or amidoamines and mixtures of these tensides, from about 0.5 to about 3.0 wt. % of an organic acid selected from the group of maleic acid, lactic acid and mixtures thereof from about 0.01 to about 10 wt. % of a cationic polysaccharide and a pH in the range of from about 3.75 to about 4.75.

Likewise preferred hair treatment agents are those which contain, instead of the cationic polysaccharide, a natural, mineral or synthetic oil, fat or wax component, in particular from about 0.01 to about 10 wt. % of at least one plant oil and/or a silicone as a hair-conditioning active substance.

A further subject matter of the present disclosure is a method for strengthening the internal hair structure comprising the following steps:

i. applying a hair treatment agent to—preferably wet—dyed-blond or oxidatively coloured hair, ii. letting the agent act for a period of at least about 5 seconds, iii. optionally: rinsing out the composition with water, exemplified in that the hair treatment agent has a pH in the range of from about 3.5 to about 5 and contains—relative to its weight:

a) from about 0.01 to about 10 wt. % of a polyvalent metal salt, wherein the metal salt is selected from the group of strontium salts, zirconium salts, hafnium salts, titanium salts, tin salts, aluminium salts, bismuth salts, lanthanum maleate, lanthanum chloride and mixtures thereof, b) from about 0.01 to about 10 wt. % of an organic acid selected from the group of tartaric acid, citric acid, maleic acid, fumaric acid, salicylic acid, lactic acid, malic acid, amino acids and mixtures thereof.

In a first preferred embodiment the method comprises the following steps:

i. applying a shampoo as hair treatment agent to the wet dyed-blond or oxidatively coloured hair, ii. letting the shampoo act for a period of from about 5 seconds to about 5 minutes, iii. rinsing out the shampoo with water.

In a second preferred embodiment the method comprises the following steps i. applying a hair rinse or a hair conditioner as hair treatment agent to the wet dyed-blond or oxidatively coloured hair, ii letting the hair rinse or hair conditioner act for a period of from about 5 seconds to about 5 minutes, iii. rinsing out the hair rinse or the hair conditioner with water.

In a third preferred embodiment the method comprises the step of applying a hair (care) spray, hair gel or hair wax as hair treatment agent to the dry dyed-blond or oxidatively coloured hair A further subject matter of the present disclosure is the use of a hair treatment agent to strength the internal hair structure, in particular in the case of oxidatively damaged hair.

EXEMPLARY EMBODIMENTS

The following hair treatment agents were produced (the quantitative information here relates to wt. %):

TABLE 1

| Shampoos | | | |
|---|---|---|---|
| | Shampoo 1 | Shampoo 2 | Shampoo 3 |
| Sodium laureth sulphate | 12.5 | 14.5 | 16.5 |
| Cocamidopropyl betaine | 4.0 | 4.0 | 4.0 |
| Disodium cocoamphodiacetate | 2.0 | 2.0 | 2.0 |
| PEG-12 dimethicone | 0.5 | 0.5 | 0.5 |
| PEG-7 glyceryl cocoate | 0.5 | 0.5 | 0.5 |
| Polyquaternium-10 | 0.3 | 0.3 | 0.3 |
| Hydrogenated castor oil | 0.6 | 0.6 | 0.6 |
| Sodium benzoate | 0.5 | 0.5 | 0.5 |
| Lanthanum chloride | 1.0 | — | 3.0 |
| Lanthanum maleate | — | 1.5 | — |
| Aluminium lactate | — | — | 1.3 |
| Maleic acid | — | 2.0 | — |
| Lactic acid | 2.0 | — | 1.5 |
| NaOH for adjusting pH | + | + | + |
| Water | ad 100 | ad 100 | ad 100 |
| pH | 4.5 | 4.5 | 4.5 |

Shampoos 1 to 3 were produced by employing conventional methods of manufacture. The formulations were homogeneous after manufacture and were then storage-stable over several weeks.

DSC Measurements

Background

Hair is a keratin-containing material which has a complex morphological fine structure. For mechanical or thermal investigations the structure can be simplified as a two-phase filament/matrix composite material in which alpha helical filaments are embedded in an amorphous matrix. These two dominant compounds largely determine the mechanical properties of human hair. The values of the peak temperature provide information relating to the damage or integrity of the matrix and $\alpha$ helix. The looser (less cross-linked) is the matrix or the smaller the crystals of the alpha helical phase, the lower is the peak temperature.

Implementation

Materials

Hair strands: Alkinco 6634 (USA), natural dark European hair, A22

Equipment: Perkin Elmer DSC 8000

DSC pans: large volume (60 μl), stainless steel pans, covers and O ring (24 atm)

Pre-Treatment of Hair Strands

Three hair strands were used for each reference and each agent.

The hair strands were cleaned with SLES (approx. 3% active substance in deionized water, pH 6-7). Then all the strands except for those for the untreated reference were dyed blond once with Blond Me Lift9+, mixing ratio 1:2 (bleach powder:developer with 9% $H_2O_2$). 5 g of the mixture was applied per g of hair for 45 min. The pre-treatment was ended at least 48 hours before application of the agent.

Composition and Application of the Agent

An aqueous agent M1, containing lanthanum trichloride and lactic acid was produced. The pH value of the agent was 4.5.

An aqueous agent M2 containing 1 wt. % aluminium lactate and lactic acid was produced (please complete→see p. 18 of the presentation for Dresden). The pH of the agent was 4.5.

The hair strands were dipped in the agent for 15 minutes at room temperature. The hair was then rinsed with tap water for 20 seconds and finally dried for 15 minutes.

Measurement

All the hair strands were cut into snippets ~1 mm long. 12 aliquots per agent and reference were placed into DSC pans. After adding 50 ml of deionized water, each pan was sealed. The measurement was made in a temperature range of 100-200° C. at a heating rate of 10 Kelvin per minute. The denaturing temperature (=peak temperature) was determined.

Results

TABLE 2

Tests with lanthanum chloride

| Hair strands | Denaturing temperature [° C.] |
|---|---|
| Untreated | 152.1 |
| Dyed ultrablond | 146.0 |
| Dyed ultrablond + M1 | 150.2 |

TABLE 3

Tests with aluminium lactate

| Hair strands | Denaturing temperature [° C.] |
|---|---|
| Untreated | 156.0 |
| Dyed ultrablond | 149.3 |
| Dyed ultrablond + M2 | 152.3 |

Swelling in Water

TABLE 4

Swelling in water

| Hair strands | [%] |
|---|---|
| Untreated | 11 |
| Dyed ultrablond (4x) | 19.5 |
| Dyed ultrablond (4x) + $Al^{3+}$ | 16 |
| Dyed ultrablond (4x) + $La^{3+}$ | 13 |

Treatment of hair strands dyed ultrablond four times (see above) with aluminium cations or lanthanum cations results in a significant reduction in the swelling of the hair strands in water.

Tear Strength

Materials

Hair samples: Kerling International (Backnang, Germany), European natural hair 7/0 mixture 138; single hair Equipment:Universal-Dimensions-measuring device UDM 5000A, (Zimmer GmbH, Darmstadt, Germany)

Stress-Strain-System MTT 680 with controller UV 1000 (Dia-Stron AG, UK)

Conditioner:

Conditioner 1: Standard conditioner with pH=4.5

Conditioner 2: Standard conditioner with pH=4.5+1 wt. % of a 30% aluminium lactate solution.

Measurement of the Hair Thickness

At the beginning of the test the average cross-sectional area of each individual hair was measured at a temperature of 22° C. and a relative humidity of 50%. The data thus obtained were used to calculate the tensile strength before and after using the product.

Bleaching and Product Application

The individual wet hairs were bleached with Blond Me Lift9+, mixing ratio 1:2 (bleach powder: developer with 9% $H_2O_2$) at 32° C. (application time 45 minutes).

The fibres were rinsed with tap water for 120 seconds.

The hair fibres were then soaked in the conditioner to be studied. The application time was 20 minutes. The hair fibres were then rinsed with tap water for 60 seconds and finally dried for 60 minutes.

The entire process (bleaching and application of the conditioner) was carried out twice.

The treated hair fibres were stored for at least 48 hours.

Determination of the Breaking Stress and Breaking Elongation after Application of the Products The hair fibres were soaked in water for at least 1 hour. They were then stretched to breaking point at a constant speed of 10 mm/min. The breaking elongation (elongation at the breaking point) and the breaking stress (stress at the breaking point) were then calculated.

TABLE 5

Breaking elongation

| Hair fibre | Breaking elongation [%] |
|---|---|
| Untreated | 51.1 |
| Dyed ultrablond (2x) + C1 | 60.0 |
| Dyed ultrablond (2x) + C2 | 63.9 |

TABLE 6

Breaking stress (tensile strength)

| Hair fibre | Breaking stress [TPa] |
|---|---|
| Untreated | 2.57E−04 |
| Dyed ultrablond (2x) + C1 | 1.51E−04 |
| Dyed ultrablond (2x) + C2 | 1.75E−04 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair treatment agent for strengthening the internal hair structure with a pH in a range of from about 3.5 to about 5 comprising relative to the total quantity of hair treatment agent— a) from about 0.01 to about 10 wt. % of a polyvalent metal salt, wherein the metal salt is selected from the group of lanthanum maleate and lanthanum chloride in combination with aluminum lactate; and
b) from about 0.01 to about 10 wt. % of an organic acid selected from the group of maleic acid, lactic acid, and mixtures thereof.

2. The hair treatment agent according to claim 1, wherein the polyvalent metal salt is lanthanum chloride in combination with aluminum lactate.

3. The hair treatment agent according to claim 1, wherein the polyvalent metal salt is lanthanum maleate.

4. The hair treatment agent according to claim 2, wherein the organic acid comprises lactic acid.

5. The hair treatment agent according to claim 3, wherein the organic acid comprises maleic acid.

6. The hair treatment agent according claim 1, further comprising from about 0.5 to about 20.0 wt. % of at least one anionic tenside selected from the group of alkyl(ether)sulphates, sulfosuccinates, ethercarboxylic acids, N-acylamino acids with from about 8 to about 24 C atoms in the acyl group, (acyl)isethionates with from about 8 to about 24 C atoms in the acyl group, and mixtures of these tensides.

7. The hair treatment agent according to claim 1, further comprising from about 0.1 to about 10.0 wt. % of at least one cationic tenside selected from the group of quaternary ammonium compounds, esterquats and/or amidoamines, and mixtures of these tensides.

8. The hair treatment agent according to claim 1, further comprising at least one hair-conditioning active substance.

9. A method for strengthening the internal hair structure comprising the following steps:
  i. applying a hair treatment agent to dyed-blond or oxidatively coloured hair,
  ii. letting the agent act for a period of at least about 5 seconds,
  iii. optionally: rinsing the composition out of the hair with water,
  wherein
  the hair treatment agent has a pH in the range of from about 3.5 to about 5 and comprises—relative to its weight:
  a) from about 0.01 to about 10 wt. % of a polyvalent metal salt, wherein the metal salt is selected from the group of lanthanum maleate and lanthanum chloride in combination with aluminum lactate, and
  b) from about 0.01 to about 10 wt. % of an organic acid selected from the group of maleic acid, lactic acid, and mixtures thereof.

10. The hair treatment agent according to claim 1, further comprising a cationic polysaccharide in a weight fraction of from about 0.01 to about 10 wt. % of the total weight of the hair treatment agent.

11. The hair treatment agent according to claim 1, further comprising a cationic tenside in a weight fraction of up to 2 wt. % of the total weight of the hair treatment agent.

12. The hair treatment agent of claim 1, wherein:
  the polyvalent metal salt is present in an amount of from about 0.1 to about 7.5 wt. %;
  the organic acid is present in an amount of from about 0.1 to about 5.0 wt. %; and
  the hair treatment agent has a pH in the range of from about 3.75 to about 4.75.

13. The hair treatment agent of claim 1, wherein:
  the polyvalent metal salt is present in an amount of from about 0.5 to about 5.0 wt. %;
  the hair treatment agent further comprises at least one anionic tenside present in an amount of from about 0.5 to about 20.0 wt. % and selected from the group of alkyl(ether)sulphates, sulphosuccinates, ethercarboxylic acids, N-acylamino acids with from about 8 to about 24 C atoms in the acyl group, (acyl)isethionates with from about 8 to about 24 C atoms in the acyl group, and mixtures of these tensides;
  the organic acid is present in an amount of from about 0.1 to about 5.0 wt. %; and
  the hair treatment agent has a pH in the range of from about 3.75 to about 4.75;
  wherein all amounts are based on the total weight of the hair treatment agent.

14. The hair treatment agent of claim 1, wherein:
  the polyvalent metal salt is present in an amount of from about 0.5 to about 5.0 wt. %;
  the hair treatment agent further comprises at least one anionic tenside present in an amount of from about 0.5 to about 20.0 wt. % and selected from the group of alkyl(ether)sulphates, sulphosuccinates, ethercarboxylic acids, N-acylamino acids with from about 8 to about 24 C atoms in the acyl group, (acyl)isethionates with from about 8 to about 24 C atoms in the acyl group, and mixtures of these tensides,
  the organic acid is present in an amount of from about 0.5 to about 3.0 wt. %, and
  the hair treatment agent has a pH in the range of from about 3.75 to about 4.75;
  wherein all amounts are based on the total weight of the hair treatment agent.

15. The hair treatment agent of claim 1, further comprising a natural, mineral or synthetic oil, fat or wax component.

16. The hair treatment agent of claim 15, wherein the natural, mineral or synthetic oil, fat or wax component is present in an amount of from about 0.01 to about 10 wt. % based on the total weight of the hair treatment agent and is selected from at least one plant oil and/or a silicone as a hair-conditioning active substance.

17. The hair treatment agent of claim 1, wherein:
  the polyvalent metal salt is present in an amount of from about 0.5 to about 5.0 wt. %;
  the hair treatment agent further comprises at least one anionic tenside present in an amount of from about 0.5 to about 20.0 wt. % and is selected from the group of alkyl(ether)sulphates, sulphosuccinates, ethercarboxylic acids, N-acylamino acids with from about 8 to about 24 C atoms in the acyl group, (acyl)isethionates with from about 8 to about 24 C atoms in the acyl group, and mixtures of these tensides;
  the organic acid is present in an amount of from about 0.5 to about 3.0 wt. %;
  the hair treatment agent further comprises a cationic polysaccharide present in an amount of from about 0.01 to about 10 wt. %; and
  the hair treatment agent has a pH in the range of from about 3.75 to about 4.75;
  wherein all amounts are based on the total weight of the hair treatment agent.

18. The hair treatment agent of claim 4, wherein:
  the polyvalent metal salt is present in an amount of from about 0.5 to about 5.0 wt. %;
  the hair treatment agent further comprises at least one anionic tenside present in an amount of from about 0.5 to about 20.0 wt. % and is selected from the group of alkyl(ether)sulphates, sulphosuccinates, ethercarboxylic acids, N-acylamino acids with from about 8 to about 24 C atoms in the acyl group, (acyl)isethionates with from about 8 to about 24 C atoms in the acyl group, and mixtures of these tensides;

the organic acid is present in an amount of from about 0.5 to about 3.0 wt. %;

the hair treatment agent further comprises a cationic polysaccharide present in an amount of from about 0.01 to about 10 wt. %; and the hair treatment agent has a pH in the range of from about 3.75 to about 4.75;

wherein all amounts are based on the total weight of the hair treatment agent.

19. The hair treatment agent of claim 5, wherein:

the polyvalent metal salt is present in an amount of from about 0.5 to about 5.0 wt. %;

the hair treatment agent further comprises at least one anionic tenside present in an amount of from about 0.5 to about 20.0 wt. % and is selected from the group of alkyl(ether)sulphates, sulphosuccinates, ethercarboxylic acids, N-acylamino acids with from about 8 to about 24 C atoms in the acyl group, (acyl)isethionates with from about 8 to about 24 C atoms in the acyl group, and mixtures of these tensides;

the organic acid is present in an amount of from about 0.5 to about 3.0 wt. %;

the hair treatment agent further comprises a cationic polysaccharide present in an amount of from about 0.01 to about 10 wt. %; and the hair treatment agent has a pH in the range of from about 3.75 to about 4.75;

wherein all amounts are based on the total weight of the hair treatment agent.

* * * * *